(12) United States Patent
Elgebaly et al.

(10) Patent No.: US 8,333,987 B2
(45) Date of Patent: Dec. 18, 2012

(54) NOUREXIN-4 NANO-LIPID EMULSIONS

(76) Inventors: Salwa Elgebaly, Edgewater, MD (US); Elliott Schiffmann, Chevy Chase, MD (US); Tamer Elbayoumi, Peoria, AZ (US)

( * ) Notice: Subject to any disclaimer, the term of this patent is extended or adjusted under 35 U.S.C. 154(b) by 382 days.

(21) Appl. No.: 12/570,307

(22) Filed: Sep. 30, 2009

(65) Prior Publication Data

US 2010/0119594 A1 May 13, 2010

Related U.S. Application Data

(60) Provisional application No. 61/113,333, filed on Nov. 11, 2008.

(51) Int. Cl.
| A61K 9/127 | (2006.01) |
| G01N 33/53 | (2006.01) |
| C12Q 1/70 | (2006.01) |
| A61K 31/197 | (2006.01) |
| A61P 37/04 | (2006.01) |
| A61P 31/14 | (2006.01) |
| A61P 31/04 | (2006.01) |

(52) U.S. Cl. ............ 424/450; 435/7.21; 435/5; 514/565

(58) Field of Classification Search .................. None
See application file for complete search history.

(56) References Cited

U.S. PATENT DOCUMENTS

| 2002/0188024 A1* | 12/2002 | Chilton et al. ................. 514/560 |
| 2007/0213234 A1* | 9/2007 | Yaghmur et al. .............. 508/110 |
| 2008/0008694 A1* | 1/2008 | Elgebaly et al. ............. 424/94.1 |

OTHER PUBLICATIONS

De Paulis et al. (Journal of Allergy and Clinical Immunology 1996 vol. 98 No. 1, pp. 152-164).*

* cited by examiner

Primary Examiner — Robert A Zeman
(74) Attorney, Agent, or Firm — Latimer IP Law, LLC

(57) ABSTRACT

The present invention provides compositions and methods for identifying, monitoring, and/or treating tissue inflammation caused by diseases or injury. Inflammatory mediators from the Nourin family are provided as diagnostic markers to detect or monitor a disease or injury that results in inflammation. In addition, the Nourin family antagonist, Nourexin-4 is provided as a therapy to treat diseases or injury. Further, cyclocreatine is provided as an inhibitor of Nourin formation, which can be used as a therapy to treat injury and inflammation.

8 Claims, 6 Drawing Sheets

NOUREXIN-4 NANO-LIPID EMULSIONS

CROSS-REFERENCE TO RELATED APPLICATIONS

This application relies on the disclosure of and claims the benefit of the filing date of U.S. provisional patent application No. 61/113,333, filed on 11 Nov. 2008, the entire disclosure of which is hereby incorporated herein by reference.

BACKGROUND OF THE INVENTION

1. Field of the Invention

The present invention relates to the field of inflammation caused by injury or disease. More specifically, the invention relates to inflammatory mediators and their antagonists.

2. Description of Related Art

Uncontrolled inflammatory processes, whether initiated by infections, immunologic, or environmental factors, represent extremely explosive and potentially destructive biologic responses. Central to these inflammatory processes are the recruitment and activation of leukocytes. This activation can occur both locally within tissues, as well as systemically, e.g. as in cytokine storms. In general, a cytokine storm is induced by a viral infection (e.g., influenza flu), by a gram-negative bacterial infection (endotoxin), or in patients infected by a virus and then infected by a gram-negative bacterial infection due to a compromised immune system.

Cytokine storms result in profound local and systemic activation of the immune system and can lead to organ failure and death. A cytokine storm is the systemic expression of a healthy and vigorous immune system resulting in the release of many inflammatory mediators, including chemokines, cytokines, oxygen free radicals, digestive enzymes, and coagulation factors. Key pro-inflammatory mediators in the cytokine storm are Tumor Necrosis Factor α (TNF-α), Interleukin 1β (IL-1β), Interleukin 8 (IL-8), and Interleukin 6 (IL-6). Acute respiratory viral infection results in a cytokine storm affecting the lungs, and subsequently damages the alveoli and lung tissue. Activated immune cells release toxic substances such as free radicals and digestive enzymes, resulting in tissue necrosis and organ failure. In the absence of prompt medical intervention to stop the cytokine storm, the lung will suffer permanent damage. Deaths will usually result from multisystem organ failure and not from lung failure. Avian influenza is known to affect more organs (including the GI tract) than does ordinary influenza, which affects primarily the lung.

The Swine influenza H1N1 virus is now a prominent flu strain for which a vaccine is being tested. In the 1997 outbreak, elevated blood levels of Interleukin 6 (IL-6) and Tumor Necrosis Factor α (TNF-α), interferon-γ, and soluble interleukin-2 receptor were observed in influenza patients. In the 2003 outbreak, elevated levels of the chemokines interferon-induced protein 10, monocyte chemoattractant protein 1, and monokine induced by interferon-γ were found in infected patients three to eight days after the onset of illness. Clinical studies suggest that the innate immune responses to Avian influenza A (H5N1) may contribute to disease pathogenesis. In general, the levels of inflammatory mediators were found to be higher among patients who died than among those who survived.

There is growing concern that Avian influenza (bird flu) may again spread across the world in a pandemic that far surpasses the 1918 pandemic. Despite the threat that influenza represents, relatively little is known about the mediators and mechanisms that drive the progression of this disease, particularly the early mediators that are associated with pulmonary inflammation and loss of lung function. Central to this process is the recruitment and activation of leukocytes in the virus-infected lung. Although leukocytes, such as neutrophils, monocyte/macrophages, and lymphocytes, are generally thought to play a protective role during early infections in the form of inflammation, this inflammation when uncontrolled has the potential to totally destroy healthy tissue, including the lungs. Additionally, recruited leukocytes, such as the macrophages, can be co-opted by the influenza virus as a source/viral host for additional virus production. The Avian and Swine influenza usually begins much like more prevalent yearly influenza-fever, cough, sore throat and muscle aches, but the virus forces the immune system into overload causing organ failures and in some cases death. It is still not clear what the endogenous inflammatory mediators are that modulate the initial inflammatory responses (innate immunity) during influenza infection. Even less is known about the early immune cascade of events that tilt the balance to either immune protection with resolution and recovery or to the devastating overactive inflammatory response leading to immunopathology disease and death.

Previous studies have identified some virus-induced chemotactic factors that are associated with later stages of influenza infection, i.e. >48 hrs (e.g. Interleukin-8 (IL-8), etc.). However, no one has identified early chemotactic factors that are responsible for the initial recruitment of leukocytes seen during early stages of influenza infections in the lungs.

Clinically, vaccines and anti-viral medications are the two most common approaches generally used to prevent and treat viral infections. However, neither can control the excessive host inflammatory response, including cytokine storms, which occur secondary to viral influenza infections and can cause organ failure and death. In addition, vaccine shortages are common due to insufficient sources of viral coat materials and the cost of stockpiling enough vaccine for an entire population. Another disadvantage for both vaccinations and anti-viral medications is that viral mutations can render the drug or vaccine ineffective.

Early diagnosis in the form of a quick point-of-care test is a vital element in the defense against Swine and Avian influenza. Vaccination, drug treatment, and containment are all under consideration for Swine and Avian influenza preparedness, but their use cannot be optimized unless infection is quickly detected. Early stages of Swine and Avian flu influenza, when transmission first begins, lack distinguishing clinical symptoms from seasonal influenza and thus require a sensitive biochemical test. Because such a test will most likely be used under diverse conditions, ranging, for example, from emergency rooms to airports, it needs to be as straightforward and robust as possible.

The power of containment is still the traditional first line of defense against an epidemic, but rapid identification of infections in individuals or animals is crucial to treatment and to containment strategies. Unfortunately, current detection technologies, for example, PCR (polymerase chain reaction), viral culture, and immunoassays, do not provide a quick and easy test. PCR, which analyzes the viral genome, is the most sensitive but is slow (minimum time, two hours), requires highly trained personnel, and can miss new viral strains. Viral culture is the gold standard for diagnosis but is even slower (minimum time, several days), is more difficult to perform than PCR, and requires special high-security labs to minimize the risk of release of virions that are formed during the test. Immunoassays, like those used for the familiar home pregnancy test, give rapid results and are easy to perform but currently lack the necessary sensitivity and specificity to distinguish Swine and Avian from seasonal influenza reliably. The few such immunoassay-based tests that claim to detect Swine and Avian influenza are purportedly insensitive and are thus unlikely to pick up newly evolving strains.

In addition to viral infections, cytokine storms can also occur with bacterial infections. Sepsis is a severe systemic inflammatory response and is one example of a pathologic condition associated with cytokine storms. Sepsis is an often lethal hemodynamic collapse, which is usually the result of a super infection by gram-negative bacteria producing endotoxins. Sepsis is also classified as Septic Shock Syndrome (SSS) and is the number one cause of death in hospitals. Although a wide variety of microorganisms can cause sepsis, one of the major causes of bacterial sepsis is the Gram positive *Staphylococcus aureus* (*S. aureus*). Traditionally, methicillin-resistant *S. aureus* (MRSA) infections have been known to cause sepsis in hospitals and have been limited to immunocompromised patients or individuals with predisposing risk factors. Extensive use of antibiotics and increased numbers of drug-resistant pathogens increases the risk of sepsis in the rest of the population. Recently, there has been an alarming epidemic caused by community-acquired MRSA (CA-MRSA), which can cause severe infections that result in overactive host inflammatory response, organ failure, and even death in otherwise healthy individuals. Current treatment modalities for hospitals and CA-MRSA are of limited utility and success. Formyl peptides such as the phenol-soluble modulin 3a peptide (PSM3a) are key bacterial products secreted by *S. aureus* with leukocyte chemotactic activity (i.e., leukocyte recruitment) for phagocytic leukocytes.

Uncontrolled inflammatory processes initiated by bacteria-induced sepsis represent extremely explosive and potentially destructive biologic responses. Central to these inflammatory processes are the recruitment and activation of leukocytes that lead to tissue injury and organ failure. This activation can occur both locally within tissues, as well as systemically, e.g. cytokine storms. Some of the major pro-inflammatory cytokines involved in septic shock are Interleukin 1β(IL-1β), Interleukin 6 (IL-6), Interleukin 8 (IL-8), Interleukin 18 (IL-18), and Tumor Necrosis Factor alpha (TNF-a). These cytokine storm mediators are associated with tachycardia, hypotension, procoagulatory activities, as well as leukocyte recruitment, adhesion, and activation, which further contribute to the destruction and dysfunction of many organs. A number of studies have shown that elevated levels of these cytokines correlated with poor patient outcome.

Leukocyte chemotactic factors are potent activators/mediators of leukocytes in vitro and in vivo. Leukocyte chemotactic factors (LCF) can induce a variety of activities in leukocytes, including recruiting leukocytes from the circulation into sites of infection or tissue injury, stimulating the secretion of adhesion molecules by leukocytes and vascular endothelial cells and accordingly increasing the adhesion of cells to the sites of infection and injury, and activating leukocytes and vascular endothelial cells to release chemokines, cytokines, and toxic agents such as oxygen metabolites and digestive enzymes.

The Nourin family is comprised of unique tissue-derived inflammatory mediators released by local tissues in response to diverse types of injury and infections. These mediators are potent attractants for leukocytes and appear to be among the first compounds released by injured tissues. As an early inflammatory signal, the tissue-derived factors not only initiate the cascade of events leading to inflammation, but also amplify the response. These factors activate immune cells to release a number of cytokines, chemokines, oxidants, and proteolytic enzymes and they exhibit their activities as low and high molecular weight proteins. Specifically, Nourin stimulates neutrophils and monocytes to release adhesion molecules, chemokines, and cytokines such as LECAM, IL-8, IL-1β, and TNF-α, as well as oxidants and digestive enzymes. However, the extent of the role of Nourin family peptides in inflammation due to infection has not yet been determined.

Structurally, Nourin is a 3 KDa host-derived formyl peptide and it belongs to a family of N-formyl methionyl peptides, with a common motif of formyl-methionyl at the N-terminus. Upon cell injury (trauma) or infection-induced cell damage, Nourin released from the damaged cells binds to the formyl peptide receptor (FPR) on leukocytes and subsequently induces activation of neutrophils and monocytes. It then acts as a chemotactic factor, guiding the migration of these cells to the inflammatory site. Because Nourin is released by local tissues following injury and infections and it contributes to the induction of an inflammatory response, it can be characterized as an Alarmin, a new terminology for endogenous factors, which signal to the immune system the presence of tissue damage. Because Nourin stimulates the release of IL-8, as well other chemokines and cytokines by neutrophils and monocytes, it plays a key role not only in the initiation of tissue inflammation such as in the lung after infection, but also in the amplification of circulating inflammatory response, which leads to cytokines dysfunction (cytokine storm), organ failure, and death.

Formyl peptides are not only released by host cells, but can also be bacterial products. For example, formyl peptides are key bacterial products secreted by *S. aureus* with leukocyte chemotactic activity (i.e. leukocyte recruitment) for phagocytic leukocytes. Therefore, general inhibitors of formyl peptides should inhibit both the host response of patients with sepsis, for example, and should also inhibit the pro-inflammatory formylated peptides released from bacteria.

The inventors have recognized that there exists an urgent need in the art for substances that can control the general inflammatory response when induced by injury or disease, such as viral or bacterial infections. The development of drugs that can combat both viral cytokine storms and can also be used to control sepsis is also recognized by the inventors as needed in the field. In addition, the inventors have recognized that there also exists a need for diagnostic methods for early detection of diseases or disorders involving inflammatory pathways.

SUMMARY OF THE INVENTION

The present invention provides compositions and methods for identifying, monitoring, and/or treating tissue inflammation caused by diseases or injury. Specifically, inflammatory mediators from the Nourin family can be used as diagnostic markers to detect or monitor a disease or injury. In addition, these inflammatory mediators or their antagonists can be used as a therapy to treat diseases or injury.

In a first aspect, the present invention relates generally to compositions and methods involving inflammatory mediators released early in the inflammation pathway by local tissues after bacterial and viral infection and by bacterial cells. Specifically, the present invention pertains to the leukocyte chemotactic factor Nourin released by local tissues in response to insult as an early inflammatory marker for injury or disease. As used herein, the term Nourin indicates members of the Nourin family of proteins, exemplified by Nourin-1. In one embodiment, as a host differential inflammatory response to insult, differential levels of Nourin can be used as a diagnostic marker for the early identification of diseases. For example, the host differential inflammatory response can distinguish between the highly pathogenic Avian influenza flu from the low pathogenic seasonal influenza viruses. As an early inflammatory biomarker, the "Nourin test" can also aid in the rapid detection of influenza patients who experience "overactive" inflammation in the form of severe lung inflammation and an increased circulating inflammatory response and, thus, it permits early successful clinical management.

In another aspect, the present invention provides methods comprising the use of the Nourexin-4 compound (also known as Cyclosporine H), an antagonist of Nourin, to combat uncontrolled inflammation as a result of bacterial infections. In one embodiment, methods are presented to fight *S. aureus* infections with Nourexin-4. Studies by others indicated that Cyclosporine H is a specific inhibitor for formyl peptide receptor (FPR) on leukocytes.

In an additional aspect, the invention provides methods to fight viral infections with Nourexin-4. In one embodiment, Nourexin-4 can be used against inflammation caused by the Avian influenza flu. In another embodiment, Nourexin-4 can be used against inflammation caused by Swine flu.

In yet another aspect, the present invention provides compositions of Nourexin-4. In one embodiment, these compositions comprise Nourexin-4 and liposomes. In another embodiment, these compositions comprise Nourexin-4 and micellar carriers. In still another embodiment, these compositions comprise Nourexin-4 and lipid emulsions.

In a further aspect, the invention provides compositions of cyclocreatine, which prevents the release of Nourin from injured tissues. Cyclocreatine has been shown to significantly preserve tissues against ischemic injury and markedly reduce the release of Nourin and tissue inflammation, and restore functionality post ischemia. In one embodiment, the compositions comprise cyclocreatine and liposomes. In another embodiment, these compositions comprise cyclocreatine and cyclodextrin. In another embodiment, these compositions comprise cyclocreatine and a cosolvent, which is the combination of an aqueous solution and a water soluble organic solvent/surfactant. In still another embodiment, these compositions comprise cyclocreatine, wherein the cyclocreatine is solubilized by facilitated hydrotropy.

In an additional aspect, the invention provides kits for performing the methods of the invention. Typically, the kits of the invention comprise a Nourin antagonist, such as Nourexin-4. The kits can also comprise some or all of the other reagents and supplies necessary to perform at least one embodiment of one method of the invention. For example, the kits can comprise one or more drugs that detect, monitor, or reduce inflammation. As another example, the kits can also comprise one or more drugs that inhibit activities of Nourin (e.g., to treat symptoms of infection or injury).

BRIEF DESCRIPTION OF THE DRAWINGS

The accompanying drawings, which are incorporated in and constitute a part of this specification, illustrate an embodiment of the methods of the invention, and together with the written description, serve to explain certain principles of the invention.

DETAILED DESCRIPTION OF VARIOUS EMBODIMENTS OF THE INVENTION

Figure 1:
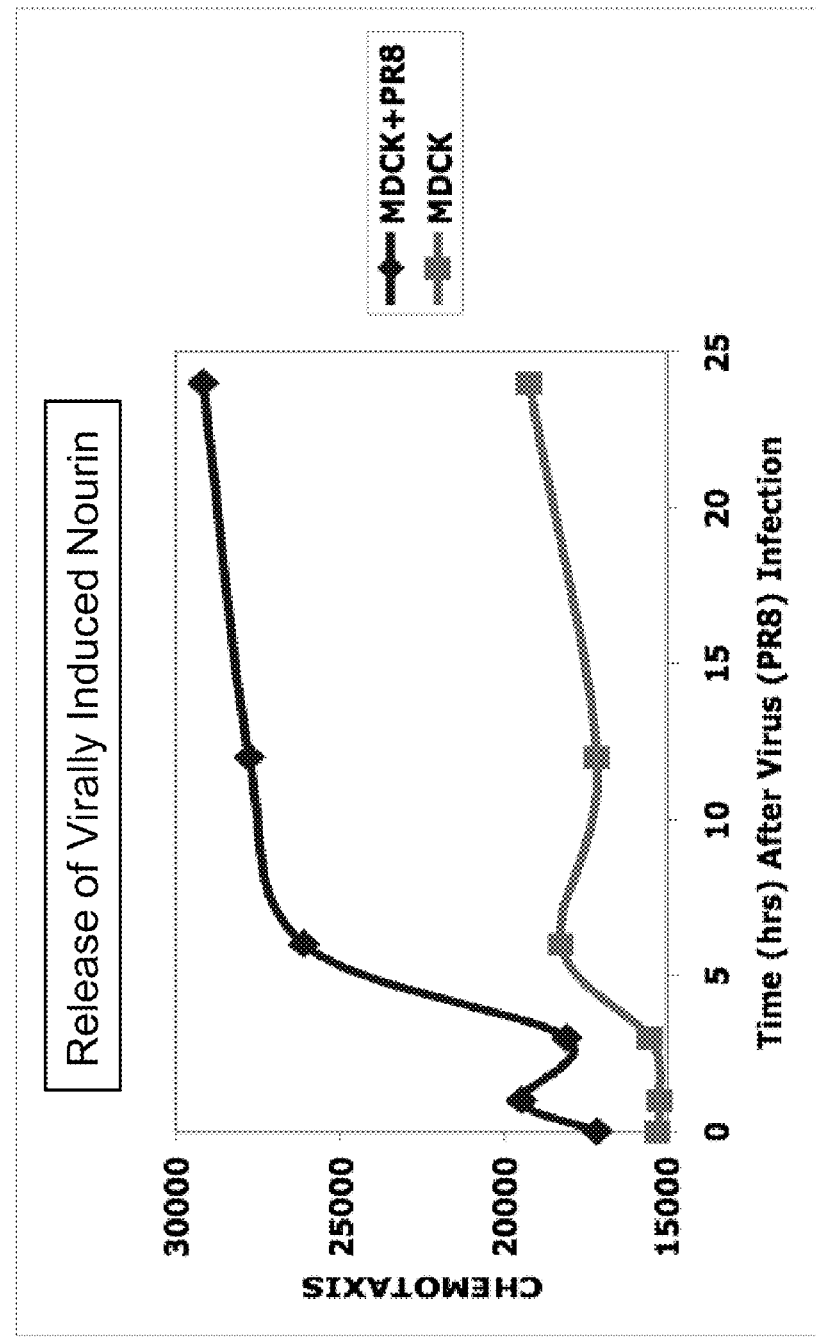
FIG. 1 illustrates the release of Nourin from Epithelial Cells in Response to H1N1 influenza virus infection.
Figure 2:
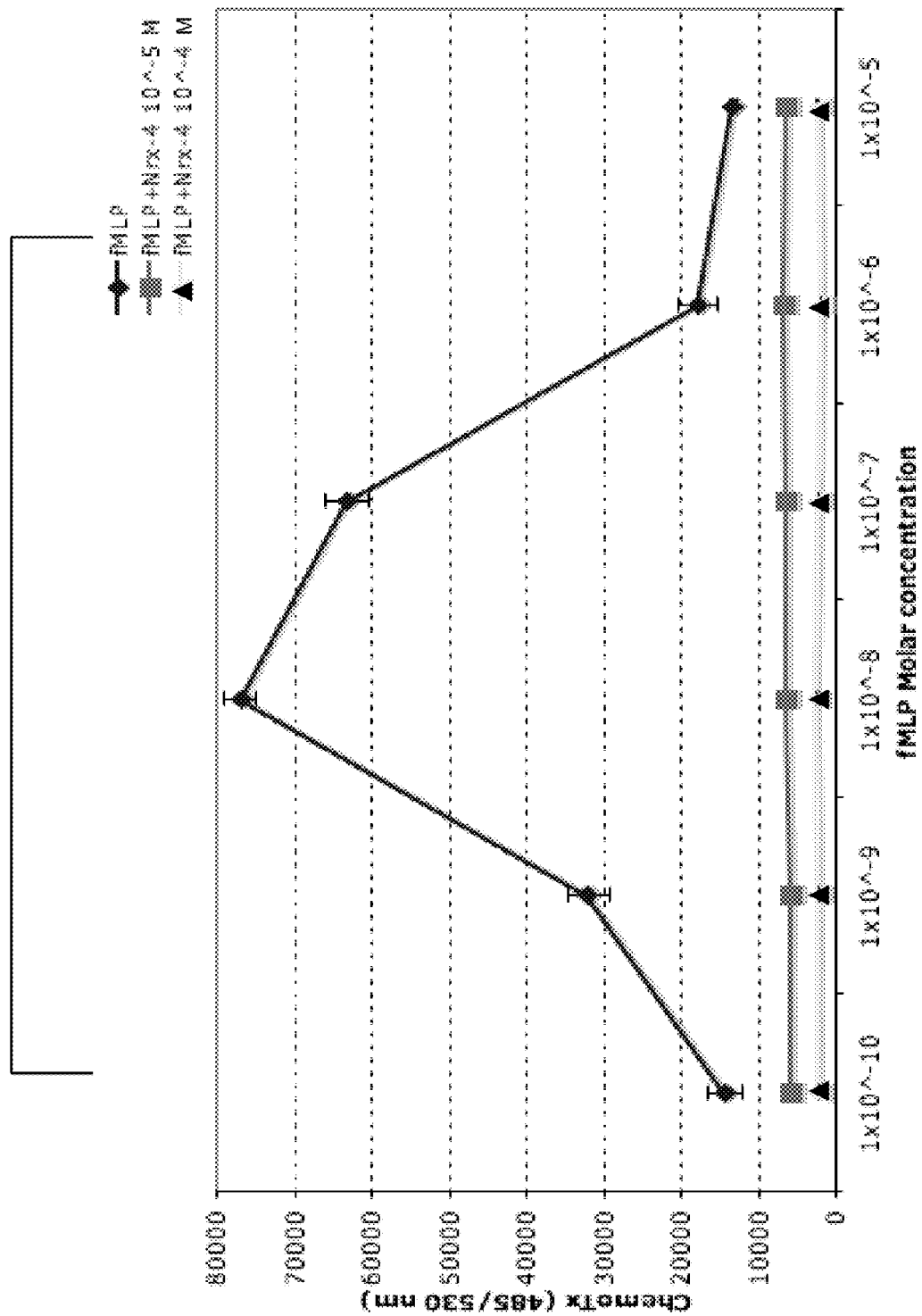
FIG. 2 shows the ability of Nourexin-4 ($10^{-5}$ M and $10^{-4}$ M) to inhibit neutrophil chemotaxis in vitro using the bacterial-derived formyl peptide f-MLP.
Figure 3:
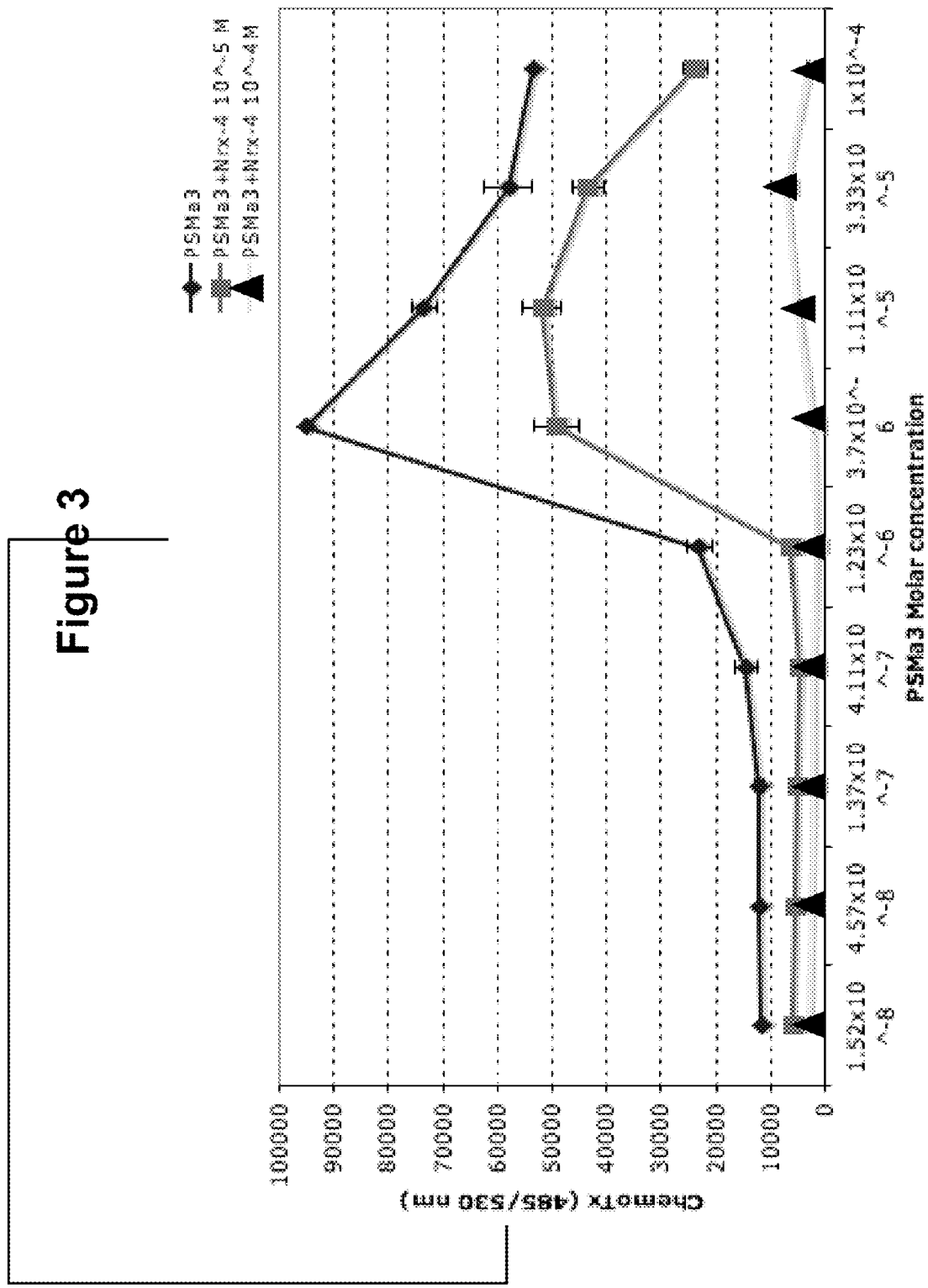
FIG. 3 depicts the ability of Nourexin-4 ($10^{-5}$ M and $10^{-4}$ M) to inhibit neutrophil chemotaxis in vitro using the *S. aureus*-derived formyl peptide PSM3a (phenol-soluble modulin 3a).
Figure 4:
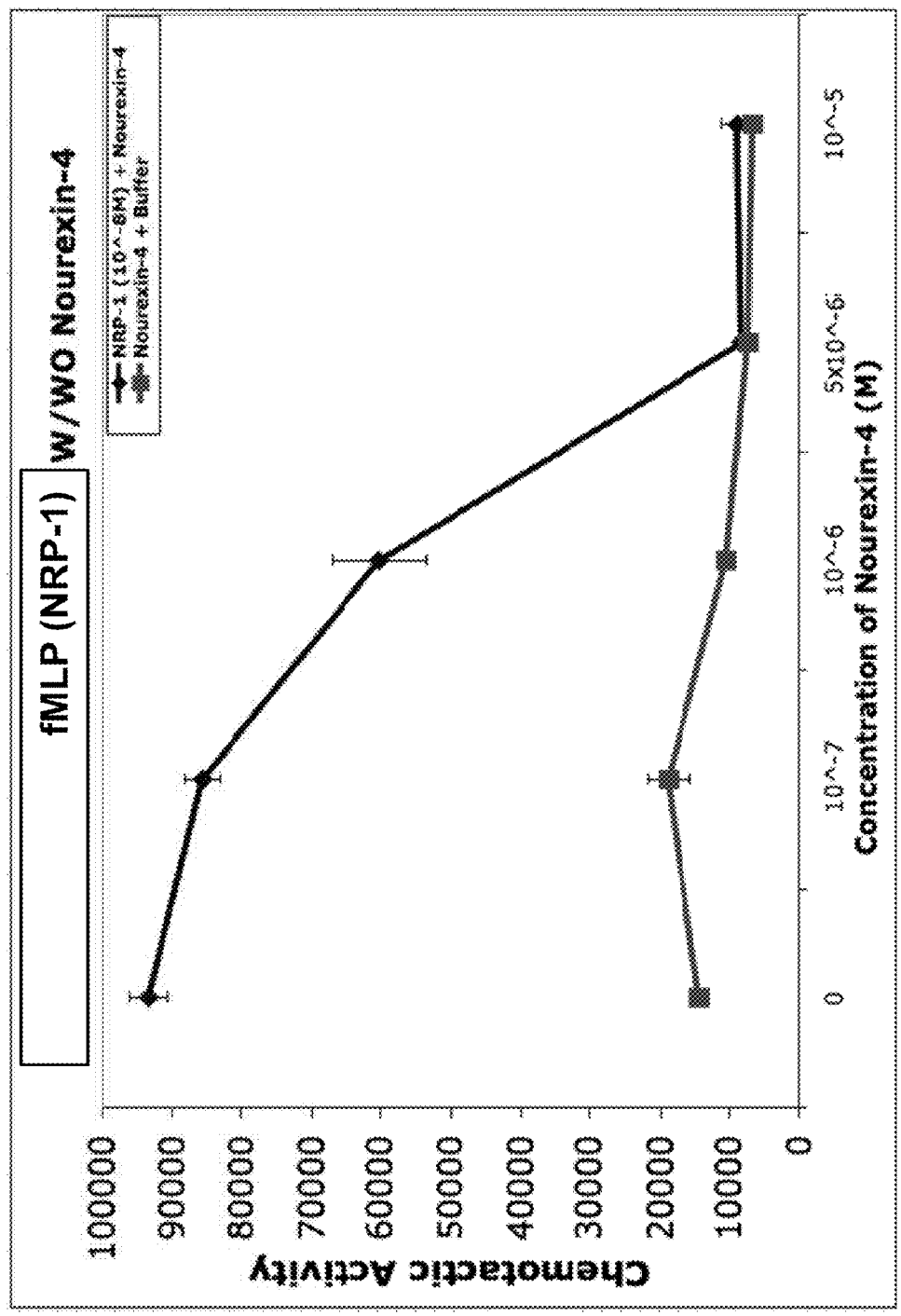
FIG. 4 illustrates a dose-response effect of Nourexin-4 ($5\times10^{-7}$ M, $5\times10^{-6}$ M, $5\times10^{-5}$ M, $5\times10^{-4}$ M) on fMLP-stimulated chemotaxis of human leukocyte cells.
Figure 5:
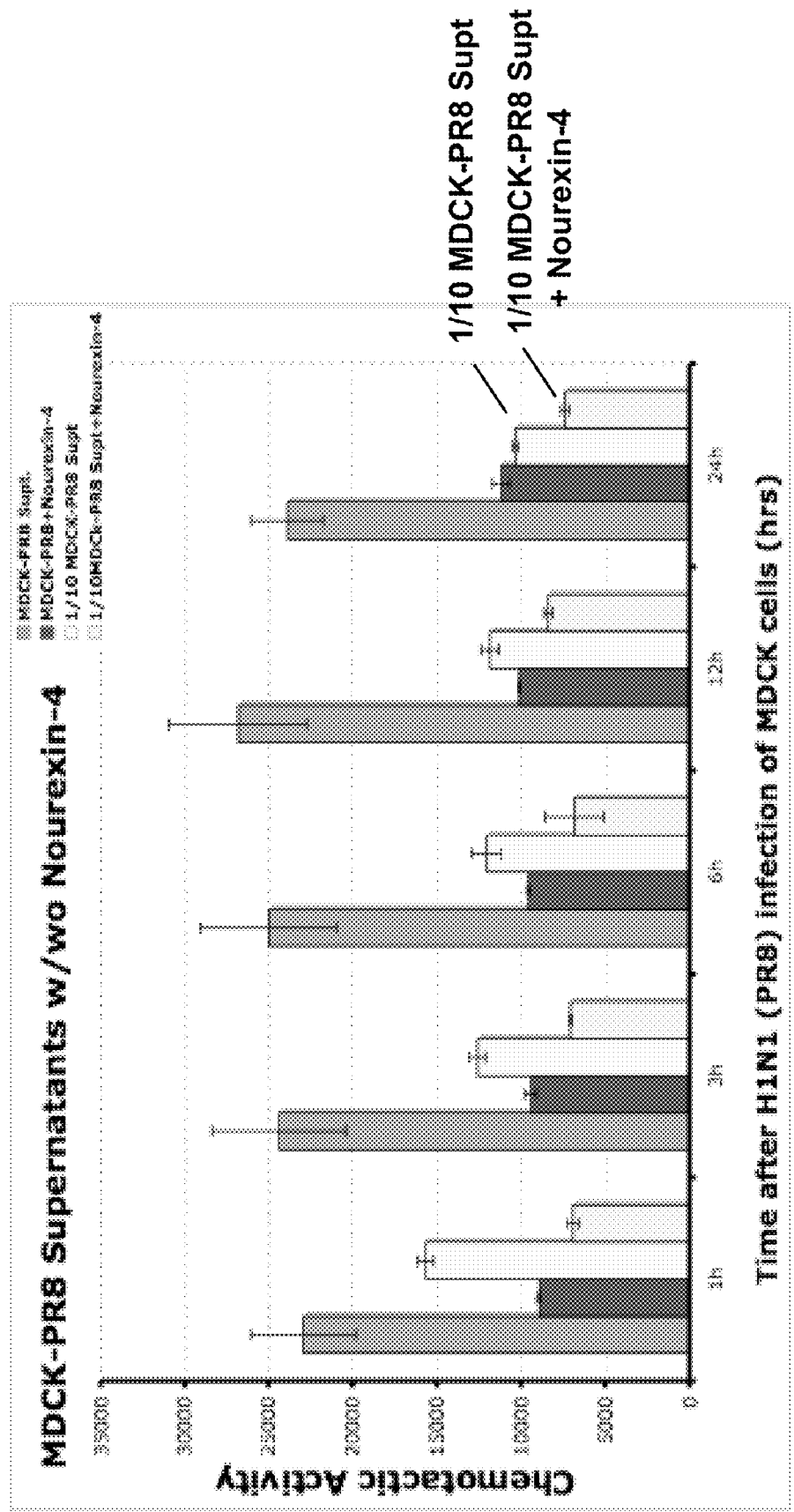
FIG. 5 shows the ability of Nourexin-4 ($5\times10^{-6}$ M) to inhibit leukocyte chemotaxis induced by Nourin detected in H1N1 infected epithelial cell culture (undiluted and 1/10 diluted in buffer).
Figure 6:
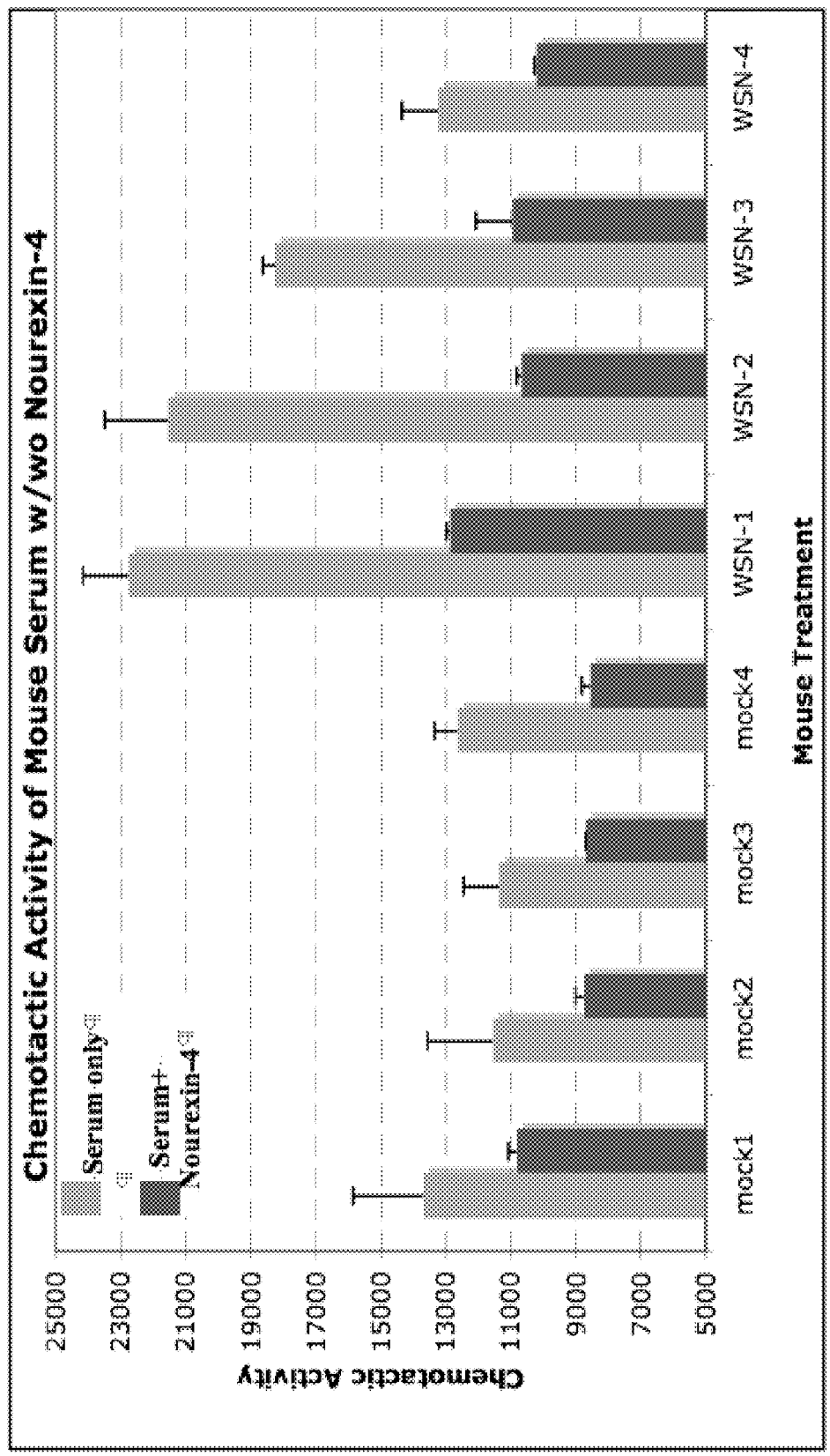
FIG. 6 depicts the ability of Nourexin-4 ($5\times10^{-6}$ M) to in vitro inhibit chemotactic activity in the blood of H1N1 influenza infected mice after 6 hours of challenge.

Reference will now be made in detail to exemplary embodiments of the invention, examples of which are illustrated in the accompanying drawings. The following detailed description is provided to assist the reader in understanding certain features and embodiments of the invention, and should not be understood as limiting the invention to any particular embodiment or combination of elements, or to any particular method steps or order of steps.

The present invention provides a method of detecting, monitoring, and/or treating a disease or disorder that is characterized by inflammation. Specifically, the present invention involves the inflammatory mediator Nourin and its antagonists. The Nourin family is comprised of unique tissue-derived inflammatory mediators released by local tissues in response to diverse types of injury and infections. "Nourin" herein refers to a family of approximately 3 KDa host-derived formyl methionyl peptides with a common motif of formyl-methionyl at the N-terminus. Upon cell injury (trauma) or infection-induced cell damage, Nourin released from the damaged cells binds to the formyl peptide receptor (FPR) on leukocytes and subsequently induces activation of neutrophils and monocytes. All members of this family are envisioned as part of the present invention, although the family member Nourin-1 is exemplified in this document. The tissue-derived Nourin released by injured or diseased local tissues include, but is not limited to, heart, vein grafts, coronary arteries, cornea, conjunctiva, retina, stomach, urinary bladder, brain, spinal cord, cultured corneal endothelial, cultured corneal epithelial cells, cultured kidney epithelial cells, and cultured bladder fibroblasts. In embodiments of the invention, antibodies, the formyl peptide Nourin receptor FPR (as a whole or soluble fractions), and antagonists to the formyl peptide Nourin are used to detect and inhibit its inflammatory activities.

In a first aspect, Nourin can be used as a diagnostic marker for the early identification of diseases and/or injury. Nourin has a unique N-terminus with potent immunostimulant effects on leukocytes. Unlike other known chemoattractants, Nourin is an early mediator released very shortly after infections and in response to reversible injury, as well as after irreversible necrotic damage as insults persist. Other known factors (formyl and non-formyl) appear much later and are released in response to irreversible or necrotic conditions. Therefore, as a crucial early signal in the cascade of events leading to inflammation and the cytokine storm, Nourin can be used as a therapeutic target to combat uncontrolled inflammatory responses secondary to injury (such as ischemia), age-related degenerative conditions, and infections. Nourin can also be used as a disease marker for early detection of various diseases.

Nourin is rapidly released within five minutes by injured local resident cells as a crucial early signal of inflammation, which recruits and activates leukocytes to sites of injury and infection. As an early response to cell injury induced by ischemia, chemical agents, infections (bacterial and viral), physical trauma, and nutritional deficiency, the Nourin chemotactic peptide is a powerful pro-inflammatory factor for a variety of leukocytes, including neutrophils and monocyte/macrophages. Specifically, Nourin stimulates leukocyte chemotaxis and activates leukocytes to release chemokines, cytokines, adhesion molecules, digestive enzymes, and free radicals characteristic of cytokine storms.

The methods of the invention generally comprise identifying injury or disease by the levels of circulating Nourin and in the tissue of a subject. Injuries, such as concussions or other internal injuries, cause local inflammation. In such cases, Nourin can be used as a biomarker for inflammation, and furthermore, for the extent of inflammation in a subject. In other embodiments, disease in a subject can also cause inflammation. For example, rheumatoid arthritis, an autoimmune disease, causes inflammation of the joints as well as inflammation in other organs in a subject. Nourin can be used as a diagnostic marker for the early identification of diseases that result in inflammation. Infection of a subject by viruses or bacteria can also result in inflammation that can be identified early by Nourin.

In one embodiment, Nourin can be used to differentiate a host inflammatory response to an infection or disease caused by different strains or causative agents. For example, a method of the invention can detect different levels of Nourin in a sample from a subject infected with a highly virulent strain of an organism as compared to a sample from a subject infected with a less virulent strain, by detecting a higher amount of Nourin in the highly virulent strain sample. Likewise, Nourin can be used to differentiate between inflammation associated with an infection, disease, or agent that is associated with morbidity but very little or no mortality compared to inflammation associated with an infection, disease, or agent that is generally considered to be associated with mortality. For example, methods are provided to distinguish the Avian influenza virus from the low pathogenic seasonal influenza virus. The Avian influenza virus results in a much more severe host inflammatory response than the less pathogenic seasonal virus. Therefore, the levels of Nourin produced early in the virus infection cycle in a subject can help determine whether the subject has been infected with the Avian influenza virus. Additionally, it has been found that there is a differential level of Nourin detected in influenza patients' samples, where patients with severe influenza infection and suffering from severe lung inflammation and/or lung failure, who are typically maintained in the Intensive Care Unit (ICU), have a much higher level of Nourin than patients with moderate influenza infection, who typically suffer only fever and wheezing, but not hospitalization in the ICU. Likewise, Nourin can be used to differentiate a host inflammatory response to Swine flu as compared to the less pathogenic seasonal virus.

Generally, the methods of identifying infection with Avian flu virus involve measuring the levels of Nourin in a subject (using for example antibodies to the formyl peptide Nourin and the formyl peptide Nourin receptor FPR as a whole or soluble fraction) and comparing the levels to levels found in other subjects. For example, the levels of Nourin in a subject can be compared to the amounts of Nourin found in subjects infected with Avian influenza virus. In addition, the amount of Nourin in a subject can also or alternatively be compared to the levels found in subjects infected with a less pathogenic influenza virus. Because Nourin is an early inflammation marker and the Nourin test is quick, results from these tests can manage the spread of the disease as well as treat subjects with Avian influenza virus quickly. In the case of a pandemic or global outbreak, a Nourin test would allow efficient use of vaccines, medicines, etc. The methods comprise not only comparing amounts of Nourin from different samples or subjects in similar tissue, but also comprise comparing amounts of Nourin in different tissues in the same subject. The Avian influenza is known to affect more organs (including the GI tract) than does ordinary influenza which affects primarily the lung. In another embodiment of the invention, the methods comprise measuring or detecting levels of Nourin in tissue that is more likely to be inflamed when infected with Avian influenza virus and less likely to show severe inflammation when infected with ordinary influenza virus.

According to the invention, a differential level of Nourin is detected in samples from subjects that are suffering from infections, injury, or other diseases/disorders associated with inflammation, as compared to samples from "normal" or "healthy" subjects or tissues. While any detectable difference in Nourin levels are encompassed by the invention, typically the difference in Nourin levels between the two samples being compared is at least 2-fold, and even up to 20-fold or more. Thus, for example, it can be a 5-fold difference, a 10-fold difference, or any particular difference within 2-fold to 20-fold. Of course, those of skill in the art will recognize that the difference should be an amount that is statistically significant for the assay involved.

In general, the methods of diagnosis or methods of identifying injury or disease associated with inflammation comprise obtaining a sample from a subject, and assaying the sample for the presence and/or amount of Nourin. Typically, the method further comprises comparing the result with the result of a separate assay performed on a different sample, such as one from a healthy subject, to determine if a difference in Nourin levels exists. Many "control" samples may be used, and those of skill in the art may select the appropriate sample based on the subject, disease/disorder, or other factors, as desired. The presence of higher Nourin levels in a test sample as compared to a control sample indicates the presence of inflammation in the subject from which the sample is taken, and thus indicates the presence of a disease, disorder, or injury. Furthermore, the relative amount of Nourin detected is an indicator of the severity of the inflammation, with higher amounts of Nourin indicating a more severe inflammation, and thus a more severe insult to the subject (e.g., as a result of a more virulent virus or bacterium).

The methods of identifying/diagnosing can be practiced in vitro, in vivo, and ex vivo. They may involve in vitro methods that comprise using Nourin as a research tool to observe the effects of inflammation on cells or observe the cells for changes in protein expression, cell morphology, or any other characteristic of interest. The methods may also be used as, or as part of, a research method to identify compounds or to determine the effect of compounds and concentrations of compounds that might reduce inflammation.

The assays to measure Nourin can vary, and any suitable assay may be used in accordance with the present invention. For example, assays that measure levels of Nourin include Western blots, antibody-based ELISA assays, FPR-based ELISA assays, immunoprecipitations, etc. In other embodiments, Nourin can be assayed by measuring changes in inflammation, changes in other inflammation mediators, changes in chemotactic activity, etc. In addition, instead of measuring actual levels of Nourin, an assay may measure the presence or absence of Nourin, which may signal the presence or absence of inflammation, an infection, or injury. Due to its relative speed and ease of use under multiple conditions, an immunoassay, such as an ELISA (antibody-based and FPR-based), is a preferred assay for detection of Nourin. Antibodies against Nourin and FPR are known in the art and can be used in immunoassays without the need to develop alternative reagents.

In one embodiment, the method provided is a method of diagnosing early inflammation in a subject due to an injury or disease. The method comprises obtaining a sample comprising biological material and measuring the amount of Nourin in the sample. Optionally, the amount of Nourin measured can be compared to the amount found in one or more control samples or expected amounts that have been determined in advance. The inflammation may be caused by a bacterial infection, such as S. aureus or E. coli infections, or the inflammation may be caused by a viral infection, such as Avian influenza virus or Swine flu virus. In embodiments, the subject of the method is human, while in other embodiments, the subject is a non-human animal.

In another embodiment, the method provided by the invention is a method of differentiating between Avian influenza virus and low-pathogenic seasonal influenza virus. The method comprises obtaining a sample comprising biological material, measuring the amount of Nourin in the sample, and comparing the amount of Nourin measured to the amounts of Nourin expected with an Avian influenza virus infection and the amounts of Nourin expected with a low-pathogenic seasonal influenza virus. The amounts detected are indicative of the type of infection. In yet another embodiment, the method differentiates between Swine flu and low-pathogenic seasonal influenza virus in the same manner.

Because our previously described tissue-derived leukocyte chemotactic factor, which we recently named Nourin, is rapidly released by local tissues in response to injury and infections and it contributes to the induction of acute and chronic inflammatory responses in vivo, it is apparent that Nourin is a key factor in the initial inflammatory response associated with immune protection post viral infection. Furthermore, because Nourin also stimulates the release of high levels of cytokine storm mediators (IL-8, IL-1$\beta$, TNF-$\alpha$, adhesion molecules, free radicals, and digestive enzymes) by neutrophils and monocytes, it is apparent that Nourin amplifies the host inflammatory response, which might lead to immunopathology and diseases characterized by cytokines dysfunction (cytokine storm), organ failure, and ultimately death.

Although not provided in graphical form herein, Applicants have developed data that demonstrates that Nourin is released in cultured epithelial cell supernatants and in mice serum only 6 hours after H1N1 influenza virus challenge. Furthermore, Applicants have found that two Nourin antagonists, Nourexin-1 (t-Boc-FLFLF) and Nourexin-4, significantly inhibited neutrophil chemotaxis induced by Nourin. The inventors thus have data showing that Nourin is a key "early" inflammatory mediator, not only in immune protection but also in cytokine storm development and immunopathology. Nourin is, thus, a crucial endogenous therapeutic target and its inhibition with the anti-inflammatory Nourexin-4 will combat virus-induced overactive inflammation, reduce organ failure, and ultimately increase patient survival.

As discussed above, the present invention is directed, in part, to use of Nourin as a marker for diseases and disorders involving inflammation, including infections by viruses and bacteria, such as influenza virus, S. aureus, and E. coli. In embodiments, Nourin is used as a diagnostic marker by detecting the presence, and preferably relative level, in a sample, the more Nourin detected indicating a more severe disease state. However, in addition to detection of Nourin alone, the invention also encompasses the detection of Nourin in combination with one or more other indicators of inflammation. For example, in addition to using Nourin as an "early" marker of tissue injury, the differential levels of these factors as well as the differential levels of other immune-cell derived inflammatory mediators can be used as indicative of disease status and severity. Two examples describing the release of various levels of the tissue derived Nourin and other inflammatory mediators in response to metabolic injury and viral infection are discussed below.

Initially, the inventors investigated the differential host inflammatory response to metabolic injury. The inventors herein show a differential response of the levels of the Nourin chemotactic factor released by heart tissues in response to various injurious conditions. The release of Nourin by isolated hearts in the first 5 and 60 minutes of ischemia was significantly altered by the incubation conditions. As described in Table 1, the release of cardiac factor was markedly increased when non-oxygenated buffer containing dextrose was substituted with (a) oxygenated buffer containing dextrose, or (b) non-oxygenated buffer without dextrose. These data support the use of differential release of the formyl leukocyte chemotactic factor Nourin in response to diverse metabolic injury to predict the severity of disease outcome. The data further support the rapid release of the cardiac factor when the cardiac tissue experienced mild reversible damage compared to other mitochondrial N-formylmethionine chemoattractants such as ND4, ND6, and Cox1 which required disruption and degeneration of isolated myocardial mitochondria through sonication.

TABLE 1

Differential levels of the Nourin cardiac factor released by ischemic hearts in response to various injurious conditions

| | % Maximum Chemotactic Response of f-MLP (100%) | |
|---|---|---|
| | 5 Minutes | 60 Minutes |
| Non oxygenated buffer with dextrose | 25% | 65% |
| Non oxygenated buffer without dextrose | 225% | 150% |
| Oxygenated buffer with dextrose | 240% | 270% |

Based on these data, the present invention provides technology for: (1) detecting high levels of the formyl peptide Nourin in influenza samples where patients have lung inflammation characterized by leukocyte infiltration; (2) demonstrating a differential level of Nourin detected in influenza patients samples with severe influenza infection (patients suffered from lung failure and had to be maintained in ICU)—much higher levels of Nourin in these samples than in samples from patients with a more moderate infection (patients suffered fever and wheezing but no hospitalization in the ICU); (3) demonstrating that the formyl peptide-specific inhibitor Nourexin-4 is able to inhibit leukocyte chemotaxis in vitro induced by Nourin, as detected in severe and moderate influenza patients' samples; and (4) showing that Nourexin-4 is a potent anti-inflammatory drug to inhibit lung inflammation post viral infection, which can inhibit circulating Nourin and lung inflammation after viral infection in both the severe and moderate influenza patients.

The inventors next considered the role of low levels of pro-inflammatory mediators released by the sublethal influenza virus H1N1. Specifically, in a study by others, volunteers were infected with the H1N1 influenza virus and followed daily for 8 days. IL-1β, IL-2, IL-6, IL8, IFN-α, TGF-B, TNF-α were measured daily in serum, plasma, and nasal wash fluid. IL-6 (450 pg/ml) and IFN-α (150 pg/ml) levels in nasal lavage fluids peaked early (day 2) and correlated directly with viral titers, temperature, mucus production, and symptom scores. IL-6 (6 pg/ml) was elevated after two days in serum, while INF-α (1.25 pg/ml) peaked after three days in serum. TNF-α (250 pg/ml) peaked after four days in nasal lavage fluids when viral shedding and symptoms were subsiding. IL-8 (9,000 pg/ml) peaked late in nasal fluids in the illness course at days 4-6 and correlated only with lower respiratory symptoms which also occurred late. None of the IL-1β, IL-2, and TGF-B levels increased significantly. It has already been shown that the early appearance of IL-6 and IFN-α are key factors both in symptom formation and host defense in influenza.

The inventors next considered the high levels of pro-inflammatory mediators released by the lethal influenza virus H5N1. The effect of lethal and sublethal influenza A viruses on the levels of TNF-α and other cytokines released by macrophages and alveolar/bronchial epithelial cells were studied by others, and the results analyzed by the present inventors. First, the levels of TNF-α were considered. Significant release of TNF-α in cultured supernatant solutions were detected from macrophages incubated with the lethal virus 486/97 (H5N1/97), W312/97 (H6N1), and G1/97 (H9N2) from 12-36 hours. These lethal viruses induced very high levels of TNF-α by 12-36 hours (550-690 ng/ml) during incubations. Sublethal viruses Y280/97 (H9N2), 54/98 (H1N1), and 437-6/99 (H5N1), on the other hand induced very little TNF-α when incubated with macrophages for 12-36 hours. The authors then studied the ability of the lethal and sublethal influenza A viruses to release TNF-α after 6 and 12 hours of incubation with macrophages in comparison to endotoxins treatments. As described here, the lethal 486/97 (H5N1/97) and G1/97 (H9N2) influenza viruses and endotoxin treatments released significantly higher levels of TNF-α (300-560 ng/ml) compared to the sublethal (15-90 ng/ml) viruses Y280/97 (H9N2), 54/98 (H1N1), and 437-6/99 (H5N1). Interestingly, the inventors have similarly shown that the tissue-derived Nourin stimulates the release of 400 ng/ml TNF-α by human peripheral monocytes after only about 4 hours of incubation. The data is presented in Table 2.

TABLE 2

TNF-α (ng/ml) Released by Macrophages

| | | 6 hours | 12 hours |
|---|---|---|---|
| Y280/97 (H9N2) | Seasonal FLU | 20 | 30 |
| 54/98 (H1N1) | Seasonal FLU | 15 | 20 |
| 1174/99 (H3N2) | Seasonal FLU | 15 | 90 |
| 486/97 (H5N1/97) | Avian FLU | 300 | 310 |
| G1/97 (H9N2) | Avian FLU | 450 | 560 |
| LPS: 10 ug/ml | | 380 | 300 |
| Mock | | 0 | 0 |

The inventors additionally considered the role of IP-10. Four types of lethal and sublethal influenza A viruses were tested for their ability to stimulate the release of IP-10 (interferon-gamma-induced protein-10) from bronchial and alveolar epithelial cells. As described here, over 10 fold increase in IP-10 by 24 hours between the levels induced by the lethal H5N1 (1750-2575 pg/ml) and seasonal H1N1 (150 pg/ml) influenza virus. Also significant difference is seen earlier by 6 hours. Tables 3 and 4 report the inventors' discoveries.

TABLE 3

IP-10 (pg/ml) (interferon-gamma-induced protein-10) Alveolar Epithelial Cells

| | | 3 hours | 6 hours | 24 hours |
|---|---|---|---|---|
| 54/98 (H1N1) | Seasonal FLU | 0 | 80 | 150 |
| 483/97 (H5N1/97) | Avian FLU | 0 | 400 | 1750 |
| 1194/04 (H5N1/04) | Avian FLU | 0 | 1000 | 2575 |
| 3046/04 (H5N1/04) | Avian FLU | 0 | 800 | 2000 |
| Mock | | 0 | 0 | 0 |

TABLE 4

IP-10 (pg/ml) (interferon-gamma-induced protein-10) Bronchial Epithelial Cells

| | | 3 hours | 6 hours | 24 hours |
|---|---|---|---|---|
| 54/98 (H1N1) | Seasonal FLU | 0 | 0 | 200 |
| 483/97 (H5N1/97) | Avian FLU | 0 | 0 | 1700 |
| 1194/04 (H5N1/04) | Avian FLU | 0 | 500 | 2200 |
| 3046/04 (H5N1/04) | Avian FLU | 0 | 250 | 1500 |
| Mock | | 0 | 0 | 0 |

The inventors also considered the role of IL-6. In a study by others, four types of lethal and sublethal influenza A viruses were tested for their effect to stimulate the release of IL-6 by bronchial and alveolar Epithelial Cells. Unlike the high differential response observed with in IP-10 (over 10 fold increase) by 24 hours between lethal H5N1 and seasonal H1N1 influenza virus, the study reported only over 2 fold increases with IL-6.

TABLE 5

IL-6 (pg/ml) Released by Bronchial Epithelial Cells

| | | 3 hours | 6 hours | 24 hours |
|---|---|---|---|---|
| 54/98 (H1N1) | Seasonal FLU | 10 | 40 | 65 |
| 483/97 (H5N1/97) | Avian FLU | 20 | 65 | 150 |
| 1194/04 (H5N1/04) | Avian FLU | 25 | 65 | 180 |
| 3046/04 (H5N1/04) | Avian FLU | 10 | 35 | 140 |
| Mock | | 15 | 10 | 25 |

TABLE 6

IL-6 (pg/ml) Released by Alveolar Epithelial Cells

| | | 3 hours | 6 hours | 24 hours |
|---|---|---|---|---|
| 54/98 (H1N1) | Seasonal FLU | 90 | 80 | 150 |
| 483/97 (H5N1/97) | Avian FLU | 170 | 120 | 310 |
| 1194/04 (H5N1/04) | Avian FLU | 170 | 190 | 410 |
| 3046/04 (H5N1/04) | Avian FLU | 100 | 80 | 380 |
| Mock | | 50 | 35 | 40 |

Based on the inventors' own studies and their analysis of work done by others, the tissue-derived Nourin can thus can be used as an early marker of cell injury and for early detection of diseases (i.e., risk factor and disease marker). The levels of the factor (measured by the low and high molecular weight active complex of Nourin) can be determined in samples including but not limited to whole blood, plasma, serum, tears, tissue samples, tissue homogenate, spinal fluids, ocular samples, and urine, etc., using standard immunoassays, mass spectrum technique, protein activity, and by measuring gene expression, among other things. A combination of such measurements can also be used. In addition, radiolabeled antibodies and FPR to Nourin can be used both in vitro and in vivo to identify the location and degree of tissue injury and inflammation as risk factor and disease marker.

The invention also encompasses the use of Nourin as an immunostimulant or immunopotentiator, particularly for diseases and disorders involving inflammation, such as infections with influenza viruses and certain bacteria, including, but not limited to, *Staphylococcus* and enteric gram negative bacteria, such as *Escherichia*. While the above disclosure focuses on the role of Nourin in deleterious physiological processes, it is also recognized herein that Nourin can play an important role in normal physiological response to injury, infection, disease, and generally disorders involved with inflammation. For example, in addition to the crucial role of Nourin as an important inflammatory mediator and its deleterious effects leading to uncontrolled inflammation, the peptide may have an anti-infection role. Medical applications may, therefore, include the use of Nourin to enhance the immune defense system to fight infections. Furthermore, Nourin can be used in protection against cancer. Recent data have expanded the concept that inflammation is a critical component of tumor progression. Many cancers arise from sites of infection, chronic irritation, and inflammation. It is now becoming clear that the tumor microenvironment, which is largely orchestrated by inflammatory cells, is an indispensable participant in the neoplastic process, fostering proliferation, survival, and migration. In addition, tumor cells have co-opted some of the signalling molecules of the innate immune system, such as selectins, chemokines, and their receptors for invasion, migration, and metastasis. These insights are fostering new anti-inflammatory therapeutic approaches to cancer development. Nourin, and Nourin in conjunction with other compounds, can be used as a part of treatment for cancers. On the other hand, one must not cause too much disability to the immune system. Bacteria often find "privileged" sites in tumor tissue, and this emphasizes the positive role Nourin may have in host defense. Delivery of Nourin directly to tumor tissues or pre-tumorous tissues can be performed to effect treatment.

Nourin can also play a role in enhancing wound healing. Cutaneous wound healing is generally divided into three phases: inflammation, granulation tissue formation, and wound healing. The Nourin family consists of unique tissue-derived inflammatory mediators that are released by local tissues in response to injury. These mediators are potent attractants for leukocytes and appear to be among the first compounds released by injured tissues. As early inflammatory signal, the tissue-derived Nourin not only initiate the cascade of events leading to inflammation, but also amplify the response. Nourin activates immune cells to release a number of cytokines such as IL-1β, IL-8, TNF-alpha, oxidants, and proteolytic enzymes. Therefore, Nourin is beneficial in enhancing wound healing in conditions where early inflammatory response after wound healing is impaired.

In general, the healing of wounds caused by accident, assault, and surgical operations has always been a central consideration in surgical practice because any breach in continuity of skin or mucous membrane exposes the deeper tissues to the danger of infections. The understanding of the mechanism of wound healing has increased dramatically during last few years. Today wound healing abnormalities are among the greatest causes of disability and deformity. Wound healing involves multiple complicated events. It is the amount and quality of scar tissue and ultimately its remodelling that is of greater importance. The understanding of this process of wound healing and factors affecting it forms the basis of any surgical procedure.

The cellular elements important in the inflammatory phase of wound healing are the polymorphonuclear leukocyte (PMN) and the monocyte or macrophage. The PMN is short lived, and though initially the predominant cell type, is largely replaced by the macrophage by the fifth day after wounding. The prime PMN function is one of the phagocytosis and killing of contaminant bacteria. Macrophage helps in bacterial phagocytosis and tissue debridement. This cell has an important function in directing the subsequent course of wound healing. After activation in the wound, these cells release proteases and vasoactive peptides, as well as growth and chemotactic factors for fibroblasts and endothelial cells. Inflammation and particularly macrophages therefore play a critical role in the wound healing scenario. Vasoactive, chemotactic, proliferative and other factors are produced from a variety of inflammatory pathways (such as kinins and complement cascades) and activated cells (such as platelets and macrophages). These factors are active in stimulating chemotaxis and proliferation of fibroblasts, endothelial and other cells.

In another general aspect, the present invention provides methods comprising the use of the Nourexin-4 compound, an antagonist of Nourin, to combat uncontrolled inflammation. As such, the invention provides methods of reducing or eliminating the effects of Nourin on the inflammatory response. The methods of the invention generally comprise contacting at least one cell with Nourexin-4. The methods thus can be practiced in vitro, in vivo, and ex vivo. They accordingly may be practiced, for example, as a research method to identify compounds or to determine the effects of compounds and concentrations of compounds, as a therapeutic method of treating a disease or disorder involving an inflammatory pathway, and as a method to prevent a disease or the symptoms of the disease. In addition, the methods may treat the symptoms of the disease or disorder rather than treat the disease or disorder itself.

In embodiments where the method is a method of treating, it can be a method of therapy (e.g., a therapeutic method) in which the amount administered is an amount that is effective for reducing or eliminating a disease or disorder (e.g., symptoms from an injury) associated with inflammation due to the activity of Nourin. Alternatively, the method may not reduce or eliminate the disease or disorder, but may cause a detectable change in at least one clinical symptom of the disease or disorder. In embodiments where the method is a method of prevention, the amount is an amount sufficient to prevent the disease or disorder or symptoms of the disease or disorder from occurring or sufficient to reduce the severity of the disease or disorder or symptoms of the disease or disorder if it does occur.

In embodiments where the methods involve a subject or patient, the individual may be a human or other mammal, including, but not limited to a rodent (e.g., mouse, rat, rabbit), a canine (e.g., a dog), a feline (e.g., a cat), an equine (e.g., a horse), an ovine (e.g., a sheep), a porcine (e.g., a pig), or a bovine (e.g., a cow or steer). The subject can be any other animal such as a bird, reptile, amphibian, or any other companion or agricultural animal. The invention thus has applicability in both human medical and animal veterinarian fields.

As used herein, a "sufficient amount" is an amount of a substance (e.g., a drug or compound) that produces a desired detectable change in at least one detectable characteristic of a disease or disorder. For example, it may be a decrease in inflammation, whether local or systemic. Alternatively, it may be stimulation of the immune system to fight infection, disease, or wound healing.

In exemplary embodiments, a sufficient amount of Nourexin-4 is an amount that is adequate to decrease the amount of detectable inflammation caused by a disease, disorder, or injury. The sufficient amount of Nourexin-4 will vary depending on the kind of subject, the kind of disease or injury, and other variables. Those of skill in the medical arts are fully capable of determining the appropriate amount for each given set of circumstances. In general, a dosing of about 0.01 ng to about 1 g, such as about 0.05 ng, 0.1 ng, 0.5 ng, 1 ng, 10 ng, 50 ng, 100 ng, 500 ng, 1 ug, 5 ug, 10 ug, 50 ug, 100 ug, 500 ug, or 1 g per kg body weight per administration should be effective in providing the desired therapeutic or prophylactic result. For example, it could be 7-25 mg Nourexin-4 per kg patient body weight. Stated in other terms, Nourexin-4 can be administered in an amount to achieve a concentration in the patient's body that ranges from about $10^{-6}$ M to about $10^{-5}$ M, such as from about $0.6-2.1\times10^{-5}$ M, a range that falls within the effective concentrations of Nourexin-4 in inhibiting chemotaxis to Nourin-related peptides (see FIGS. 3-6). In preferred embodiments, the amount of Nourexin-4 administered is greater than 500 ug per dose for a human. Of course, injection or infusion amounts will tend to be on the lower end of the range while oral administration amounts will tend to be on the upper end. Amounts may be higher when the method is practiced in vitro or ex vivo because excess compound may be easily removed at any time by washing, etc.

In another general aspect, the methods of the invention comprise the use of Nourexin-4 to combat uncontrolled inflammation caused by bacterial infections. Because Nourin is an early inflammation mediator, its antagonist, Nourexin-4 can be used to reduce or eliminate the levels of inflammation. Therefore, the invention provides methods to combat excessive inflammation and protect subjects from damaging effects of the bacterial-induced host inflammatory response, and decrease morbidity and mortality in bacterial-infected patients. In one non-limiting embodiment, the bacterial infection is an infection with *S. aureus*. In another non-limiting embodiment, the bacterial infection is an infection with *E. coli*.

In a preferred embodiment, the methods presented comprise the ability of Nourexin-4 to fight *S. aureus* infections, one of the major causes of bacterial sepsis. The methods of the invention generally comprise contacting at least one cell with at least one molecule of Nourexin-4. In embodiments, the methods comprise contacting a sample with Nourexin-4 in a sufficient amount to reduce or eliminate inflammation. Preferred embodiments thus comprise contacting at least one cell with at least two molecules of Nourexin-4. While interesting from a scientific standpoint, the precise ratio of Nourexin-4 to cell need not be determined with precision. Rather, it is sufficient that a desired result be achieved by exposure of one or more cells to an adequate amount of Nourexin-4.

In yet another general aspect, the invention provides methods to reduce, eliminate, or treat inflammation caused by an injury or disease, whereby the inflammation is caused by a viral infection. Similar to the inflammatory pathway discussed above for bacterial infections, Nourin is an early inflammatory mediator in subjects infected with some viral infections. Therefore, Nourexin-4 can be used to combat inflammation as a result of some viral infections. In a preferred embodiment, the inflammation is caused by Avian influenza virus. In other embodiments, the inflammation is caused by Swine influenza virus. In exemplary embodiments, the subject is human.

The act of administering Nourexin-4 can be any act that provides the Nourexin-4 to a subject such that it can function for its intended purpose. For example, administering can be by injection or infusion. It can thus be an intramuscular, intraperitoneal, subcutaneous, or intrathecal injection, or a slow-drip or bolus infusion. Other non-limiting examples of methods of administration include topical administration, such as by way of lotions, salves, or bandages, often on intact skin but also through open wounds, lesions, or sores. Yet other non-limiting examples include administration through mucous membranes, oral ingestion, sublingual absorption, and rectal or vaginal delivery. The vehicle of delivery may be in any suitable form, such as the form of an oral solution, gel, tablet, capsule, powder, suppository, infusible, lozenge, cream, lotion, salve, inhalant, or injection. Nourin antibodies and receptor (FPR) can also be used through dialysis to remove circulating Nourin and control inflammation.

According to embodiments of the method, the method can comprise repeating the act of contacting (e.g., administering) Nourexin-4 with the sample. In embodiments relating to administering the Nourexin-4 to subjects, repeating the administration can include one or more administrations in addition to the original administration. The amount to be administered to each subject will vary depending on usual factors taken into consideration for dosing of pharmaceuticals, such as weight, general health, and metabolic activities of the patient. Likewise, the mode of administration (e.g., injection, oral administration) will be taken into account when determining the proper amount of Nourexin-4 to administer per dose.

In some instances, it might be desirable to provide multiple, low doses of Nourexin-4 to an individual. In such cases, the method may comprise two or more administrations of less than the total effective amount, where the amount ultimately administered is an effective amount. Likewise, multiple administrations of an effective dose may be desirable where the second or subsequent administration is performed at a time well separated from the first administration.

Furthermore, where multiple administrations are performed, different modes of administration may be used. For example, if two doses are administered, one can be an injection whereas the other can be oral. In addition, if three or more doses are administered, two or more may be by the same mode, while the remaining may be from one or more different mode, in any combination, number, and order. Of course, where multiple administrations are used, each administration may be by a different mode. The mode of administration, the number of times it is repeated, and the sequence of modes of administration may be selected by those of skill in the art based on numerous considerations, and such selection is well within the abilities of those of skill in the art.

The method can also be practiced in vitro which means that contacting at least one cell with at least one Nourexin-4 molecule can occur in a petri dish, a test tube, an IV tube, or any other container applicable for contacting. When practiced in vitro, it may be a method for identifying parameters that are useful in in vivo treatment regimens. For example, the method can be practiced to study the effects of combinations of Nourexin-4 with other drugs on cells.

In another general aspect, the present invention provides new formulations or compositions of Nourexin-4. The invention envisions the compositions used in any of the methods described herein. Due to the highly lyophilic nature of cyclosporines, their parenteral or enteral administration requires the development of very complex pharmaceutical formulations, mainly in the form of oil-based emulsions/lipid suspensions. These complex formulations sometimes have precarious stability, are delicate to handle, and are sources of adverse side effects.

The present invention provides a lipid-based composition of Nourexin-4. In an embodiment, this Nourexin-4 dispersion comprises a co-solvent and tocopherol, stabilized by biocompatible amphiphilic PEGylated or non-PEGylated surfactant blend, as a vehicle or carrier for poorly-water soluble therapeutic drugs, which is substantially ethanol free and which can be administered to animals or humans in an outer aqueous phase by various routes. The oily/lipidic component forms nano-bubbles of a diameter less than 200 nm, to allow for filter sterilization, and is surrounded by emulsifier in weight ratios ranging between 0.25:1 to 1:1 of the amphoteric polymeric-lipidic emulsifier. These dispersed nano-particles can incorporate a diglyceride or a triglyceride, containing oleic acid and/or linoleic acid or other polyunsaturated fatty acid with carbon chain length ranging from 14 to 22. Also included in this oily phase can be PEGylated vitamin E. PEGylated α-tocopherol are polyethylene glycol subunits attached by a succinic acid diester at the ring hydroxyl of vitamin E which serve as a secondary surfactant, stabilizer and a secondary solvent in emulsions of α-tocopherol. Specific formulations can change the delivery time into cells, change the uptake time of certain cells, and affect the toxicity profile of the drug.

In one embodiment, the Nourexin-4 therapeutic formulation comprises phosphatidylcholine, cholesterol, dimyristoylphosphatidylglycerol, triolein, and Nourexin-4 in molar ratios from about 10 to 36 parts phosphatidylcholine, from about 0.25 to 2.3 parts cholesterol, from about 1.5 to 4.5 parts dimyristoylphosphatidylglycerol, from about 0.5 to 1.5 parts triolein, and from about 0.05 to 1.5 parts Nourexin-4. For example, the Nourexin-4 therapeutic formulation comprises phosphatidylcholine, cholesterol, dimyristoylphosphatidylglycerol, triolein, and Nourexin-4 in molar ratios from about 15 to 31 parts phosphatidylcholine, from about 0.35 to 2.1 parts cholesterol, from about 2.0 to 4.0 parts dimyristoylphosphatidylglycerol, from about 0.7 to 1.3 parts triolein, and from about 0.08 to 1.3 parts Nourexin-4. In still another example, the Nourexin-4 therapeutic formulation comprises phosphatidylcholine, cholesterol, dimyristoylphosphatidylglycerol, triolein, and Nourexin-4 in molar ratios from about 20 to 25 parts phosphatidylcholine, from about 0.4 to 1.8 parts cholesterol, from about 2.5 to 3.5 parts dimyristoylphosphatidylglycerol, from about 0.9 to 1.1 parts triolein, and from about 0.09 to 1.2 parts Nourexin-4. In specific examples, the Nourexin-4 therapeutic formulation comprises phosphatidylcholine, cholesterol, dimyristoylphosphatidylglycerol, triolein, and Nourexin-4 in molar ratios of about 21:0.5:3:1:0.1 to about 21:1.5:3:1:0.1 and about 24:0.5:3:1:0.5 to about 24:1.5:3:1:0.75. The formulations enhance the drug amount delivered and efficacy of the immunosuppressive agents, and potentially reduce diffused toxicity and adverse effect of the cyclosporin drug.

In another embodiment, the invention provides a liposomal formulation of phosphatidylcholine, cholesterol, phosphatidylserine, and triolein in molar ratios from about 3.5 to 15 parts phosphatidylcholine, from about 1.5 to 7.5 parts cholesterol, from about 0.5 to 1.5 parts phosphatidylserine, and from about 0.25 to 1.5 parts triolein. For example, the liposomal formulation provides phosphatidylcholine, cholesterol, phosphatidylserine, and triolein in molar ratios from about 5 to 13 parts phosphatidylcholine, from about 2.0 to 6.5 parts cholesterol, from about 0.7 to 1.3 parts phosphatidylserine, and from about 0.35 to 1.3 parts triolein. In another example, the liposomal formulation provides phosphatidylcholine, cholesterol, phosphatidylserine, and triolein in molar ratios from about 6 to 11 parts phosphatidylcholine, from about 2.5 to 5.5 parts cholesterol, from about 0.9 to 1.1 parts phosphatidylserine, and from about 0.45 to 1.1 parts triolein.

In a specific example, the invention provides a liposomal formulation of phosphatidylcholine, cholesterol, phosphatidylserine, and triolein in molar ratios of about 7:3:1:0.5 to about 10:5:1:1 (mol/mol). This composition allows liposomes to efficiently incorporate the Nourexin-4 cyclosporine structure and to be readily taken up by the reticuloendothelial system (RES) (liver and spleen) for faster delivery to hepatocytes.

In still another embodiment, the invention provides a liposomal formulation of phosphatidylcholine, cholesterol, phosphatidylethanolamine, and triolein in molar ratios from about 3.5 to 15 parts phosphatidylcholine, from about 1.5 to 7.5 parts cholesterol, from about 0.5 to 1.5 parts phosphatidylethanolamine, and from about 0.25 to 1.5 parts triolein. For example, the liposomal formulation provides phosphatidylcholine, cholesterol, phosphatidylethanolamine, and triolein in molar ratios from about 5 to 13 parts phosphatidylcholine, from about 2.0 to 6.5 parts cholesterol, from about 0.7 to 1.3 parts phosphatidylethanolamine, and from about 0.35 to 1.3 parts triolein. In another example, the liposomal formulation provides phosphatidylcholine, cholesterol, phosphatidylethanolamine, and triolein in molar ratios from about 6 to 11 parts phosphatidylcholine, from about 2.5 to 5.5 parts cholesterol, from about 0.9 to 1.1 parts phosphatidylethanolamine, and from about 0.45 to 1.1 parts triolein. In a specific example, a liposomal formulation for Nourexin-4 is comprised of phosphatidylcholine, cholesterol, phosphatidylethanolamine, and triolein in molar ratios of about 7:3:1:0.5 to about 10:5:1:1. This composition also allows liposomes to efficiently incorporate the cyclosporine drug and to be readily taken up by the reticuloendothelial system (RES) (liver and spleen) for faster delivery to hepatocytes or to lungs.

In a different embodiment, the invention provides a liposomal formulation of phosphatidylcholine, cholesterol, phosphatidylethanolamine, and PEGylated vitamin E (TPGS) in molar ratios from about 3.5 to 15 parts phosphatidylcholine, from about 1.5 to 7.5 parts cholesterol, from about 0.5 to 1.5 parts phosphatidylethanolamine, and from about 0.25 to 1.5 parts PEGylated vitamin E. For example, the liposomal formulation provides phosphatidylcholine, cholesterol, phosphatidylethanolamine, and PEGylated vitamin E in molar ratios from about 5 to 13 parts phosphatidylcholine, from about 2.0 to 6.5 parts cholesterol, from about 0.7 to 1.3 parts phosphatidylethanolamine, and from about 0.35 to 1.3 parts PEGylated vitamin E. In another example, the liposomal formulation provides phosphatidylcholine, cholesterol, phosphatidylethanolamine, and PEGylated vitamin E in molar ratios from about 6 to 11 parts phosphatidylcholine, from about 2.5 to 5.5 parts cholesterol, from about 0.9 to 1.1 parts phosphatidylethanolamine, and from about 0.45 to 1.1 parts PEGylated vitamin E. In a specific example, a liposomal formulation is comprised of phosphatidylcholine, cholesterol, phosphatidylethanolamine, and PEGylated vitamin E in molar ratios of about 7:3:1:0.5 to about 10:5:1:1. This composition allows liposomes to efficiently incorporate the cyclosporine drug and to be less prone to uptake by the reticuloendothelial system (RES) (liver and spleen), allowing for moderate blood residence time, and for delivery into richly prefused tissues, like lungs, myocardium and cardiomyocytes, as well as gut mucosa.

In another embodiment, the invention provides a liposomal formulation of phosphatidylcholine, cholesterol, ganglioside GM, and triolein in molar ratios from about 5 to 15 parts phosphatidylcholine, from about 2.5 to 7.5 parts cholesterol, from about 0.5 to 1.5 parts ganglioside GM, and from about 0.5 to 1.5 parts triolein. For example, the liposomal formulation provides phosphatidylcholine, cholesterol, ganglioside GM, and triolein in molar ratios from about 7 to 12 parts phosphatidylcholine, from about 3.5 to 6.5 parts cholesterol, from about 0.7 to 1.3 parts ganglioside GM, and from about 0.7 to 1.3 parts triolein. In another example, the liposomal formulation provides phosphatidylcholine, cholesterol, ganglioside GM, and triolein in molar ratios from about 9 to 11 parts phosphatidylcholine, from about 4.5 to 5.5 parts cholesterol, from about 0.9 to 1.1 parts ganglioside GM, and from about 0.9 to 1.1 parts triolein. In a specific example, the cyclosporine-containing liposomal formulation comprises phosphatidylcholine, cholesterol, ganglioside GM, and triolein in molar ratios of about 10:5:1:1. This composition allows liposomes to avoid or delay the RES uptake (the so-called stealth liposomes). Moreover, this stealth design allows also for higher accumulation in readily blood-perfused inflamed tissues like infarcts and severe localized infection sites as well as tumors, in addition to more localization in lung tissues due to triglyceride content.

In still another embodiment, the invention provides a liposomal formulation of phosphatidylcholine, cholesterol, PEG2000-5000-phosphatidylethanolamine, and triolein in molar ratios from about 55 to 165 parts phosphatidylcholine, from about 2.5 to 7.5 parts cholesterol, from about 0.5 to 1.5 parts PEG2000-5000-phosphatidylethanolamine, and from about 0.5 to 1.5 parts triolein. For example, the liposomal formulation provides phosphatidylcholine, cholesterol, PEG2000-5000-phosphatidylethanolamine, and triolein in molar ratios from about 70 to 150 parts phosphatidylcholine, from about 3.5 to 6.5 parts cholesterol, from about 0.7 to 1.3 parts PEG2000-5000-phosphatidylethanolamine, and from about 0.7 to 1.3 parts triolein. In another example, the liposomal formulation provides phosphatidylcholine, cholesterol, PEG2000-5000-phosphatidylethanolamine, and triolein in molar ratios from about 90 to 130 parts phosphatidylcholine, from about 4.5 to 5.5 parts cholesterol, from about 0.9 to 1.1 parts PEG2000-5000-phosphatidylethanolamine, and from about 0.9 to 1.1 parts triolein. A specific example of this embodiment is phosphatidylcholine, cholesterol, PEG2000-5000-phosphatidylethanolamine, and triolein in a molar ratio of 110:5:1:1. This composition also allows for long-circulation liposomal carriers that can extend the circulation half life of cyclosporins, hence decreasing the frequency of injections, as well as improving the adverse toxicity profile of the drug.

Compositions may also be comprised of micellar carriers containing monoacyl phospholipids, with or without the inclusion of cholesterol and/or TPGS as co-surfactants. These compositions can improve the incorporation of the lipophilic cyclosporine structure, as well as improve the targetability and the biodistribution of the Nourexin-4 drug.

One example of a micellar formulation for improved solubilization of Nourexin-4 is comprised of MPEG2000-phosphatidylcholine, cholesterol, and TPGS in a molar ratio of about 2:1:0.25 to about 3:1.5:1. These formulations are beneficial for enhancing the drug amount delivered and efficacy of the immunosuppressive agents, and potentially reducing diffused toxicity or adverse effect of the cyclosporin drug. This stealth design also allows for higher accumulation in readily perfused inflamed tissues like infarcs and severe localized infection sites as well as tumors.

Another example of a micellar formulation for Nourexin-4 delivery is comprised of MPEG2000-phosphatidylcholine, cholesterol, and Tween 80 in molar ratios of about 2:1:0.1 to about 3:1.5:0.5. These compositions can enhance the drug amount delivered and efficacy of the immunosuppressive agents, as well as potentially reducing diffused toxicity or adverse effect of the cyclosporin drug.

Still another example of a micellar formulation for Nourexin-4 is comprised of MPEG2000 or MPEG5000-phosphatidylethanolamine, cholesterol, and solutol HS-15 in a molar ratio of about 2:1:0.1 to about 3:1.5:0.5. This composition increases the amount of solubilized drug amount, as well as masks the systemic side effects of the cyclosporine molecule.

The present invention also contemplates lipid emulsions, which can be produced on an industrial scale, are stable during storage, and are highly biocompatible. In addition, they have a high solubilizing capacity as far as lipophilic drugs are concerned because lipid emulsions possess an oil phase in particulate form, so they can dissolve large amounts of highly lipophilic drugs.

For instance, lipid/oil in water emulsions processed for nanosize ranges of about 50-200 nm are suggested by the use of high shear forces employing micro-fluidization equipments. These oil dispersions of the aqueous phase are generally comprised of a blend of unsaturated triglyceryl natural oil/lipid with a carbon chain length of 14-22, a cosolvent system for the cyclosporine drug molecular formula R—OH, R—COOH, R—COO—R, or R—CO—R, where R is a benzyl, phenyl, or aryl-containing moiety, in addition to a vitamin E or plametic/oleic derivative of ascorbate. These oil/lipid nano-droplets are comprised of the active cyclosporine drug in their core, and are stabilized in the external aqueous phase by the surface-surrounding amphiphilic pegylated or non-pegylated surfactant blend of monoacyl phospholipids, with or without the inclusion of cholesterol and/or TPGS as co-surfactants and/or polyethoxylated triglyceride oils. These systems are attractive for both improving the incorporation of the lipophilic cyclosporine structure, as well as improving the targetability and the biodistribution of the Nourexin-4 drug.

An example of a nano-sized oil-in-water emulsion formulation for improved solubilization of Nourexin-4 is comprised of weight ratios of about 20:70:10 of oil phase:saline:surfactant blend, where the oil phase is comprised of a natural oil containing oleyl and linoleyl di- and tri-glycerides of not less than 20% by weight, in addition to cholesterol or cholesteryl amine and vitamin E in a weight ratios of about 2:0.1:1 to 1:0.25:1, and up to 1:0.25:2. This composition enhances the drug amount delivered and efficacy of the immunosuppressive agents.

In another embodiment, high HLB value surfactant (equal or above 15) and/or a drug co-solvent is added to the emulsifier blend to enhance stability. In one example, submicron O/W emulsion formulation for Nourexin-4 delivery comprises weight ratios of approximately 20:70:5-10 of oil phase: saline:surfactant blend, where the oily phase is comprised of a natural oil containing oleyl and linoleyl di- and tri-glycerides of not less than 20% by weight, in addition to benzyl alcohol and/or benzyl benzoate, and vitamin E in a weight ratios of about 2:0.1:1 to 1:0.25:1, and up to 1:0.5:2. This formulation also enhances the drug amount delivered and efficacy of the immunosuppressive agents.

Another example is O/W nano-emulsion comprised of weight ratios of 20:70:5-10 of oil phase:saline:surfactant blend, where the oily phase is comprised of a natural oil containing oleyl and linoleyl di and tri glycerides of not less than 20% by weight, in addition to benzyl alcohol and/or benzyl benzoate, vitamin E in a weight ratios of about 2:0.1:1 to 1:0.25:1, and up to 1:0.25:2.the surfactant blend would contain either Tween 80 or Solutol HS-15, TPGS and/or mPEG2000-phosphatidylethanolamine in weight ratios of 0.5:1:1. These compositions improve the concentration of solubilized Nourexin-4 delivered and efficacy of the immunosuppressive agents. This stealth design also allows for higher accumulation in readily perfused inflamed tissues like infarcts and severe localized infection sites as well as tumors.

In yet another aspect, the present invention provides formulations for cyclocreatine. Due to the clear hydrophilic nature of cyclocreatine, its parenteral or enteral administration requires the development of simple yet somewhat unique pharmaceutical formulations, mainly adding some lipophilic/amphililic character to the vehicle, like facilitated combination of facilitated hydrotropes, and liposomal/lipid suspensions.

The physiologically relevant zwitterion salt of cyclocreatine is relatively highly water-soluble but poorly permeable. Therefore, sufficient drug is available in the gut lumen due to good solubility, but an absorptive transporter will be necessary to overcome the poor permeability characteristics of this compound. For effective therapy, it is necessary to deliver cyclocreatine effectively in sufficient quantities into the systemic blood stream. In addition, in order to exert its neuronprotective action, a formulation of cyclocreatine has to possess the ability to cross or permeate through cell membrane barriers, namely the blood-brain barrier. Moreover, the in vivo fate of a drug given by a particular administration route is determined by both the physicochemical properties of drug and the anatomical and physiological characteristics of the body. Most conventional drugs, once reaching the blood circulation, distribute freely throughout the body and show relatively even tissue distribution due to their low molecular weight.

The present invention provides formulations that can be used to for cyclocreatine to be effectively transported into the appropriate tissue of a subject. In one embodiment, the transporter for cyclocreatine is a liposome, which is described above in exemplary embodiments for Nourexin-4 formulations. Another embodiment is a cyclodextrin, which is a cyclic (α-1,4)-linked oligosaccharide of α-D-glucopyranose containing a relatively hydrophobic central cavity and a hydrophilic outer surface. Cyclodextrins can increase the equilibrium solubility of some hydrophilic molecules, like cyclocreatine, by forming a noncovalent inclusion complex if the molecule or a portion of the molecule (i.e., non-polar side chain or an aromatic or heterocyclic ring) is of the appropriate size to fit inside the central cavity.

Still another embodiment is the combination of an aqueous solution and a water soluble organic solvent/surfactant (i.e., a cosolvent), which is often used in injectable formulations when pH adjustment alone is insufficient for achieving the desired solution concentration. Examples of water-soluble organic solvents and surfactants envisioned in the invention include propylene glycol, ethanol, polyethylene glycol 300, polyethylene glycol 400, glycerin, dimethylacetamide (DMA), N-methyl-2-pyrrolidone (NMP; Pharmasolve), dimethylsulfoxide (DMSO), Solutol HS 15, Cremophor EL, Cremophor RH 60, and polysorbate 80. Many cosolvent formulations are marketed using rather high concentrations of organic solvent and are usually but not always diluted prior to injection. Examples of organic solvents administered parenterally, are measured $LD_{50}s$, are of 37% DMA, 30% PEG 400, 21% ethanol, 10% (ethanol/propylene glycol, 10/40), 5.7% propylene glycol, and 5.1% DMSO.

In another embodiment, the solubilization of cyclocreatine can be achieved by facilitated hydrotropy utilizing pharmaceutically acceptable excipients. Facilitated hydrotropy is a unique strategy for solubilization in which one or more completely-water-miscible cosolvents is used to solubilize a partially water miscible (often aromatic, like cycloreatine) solute, which in turn acts to further solubilize the drug. One example of facilitated hydrotropy for cyclocreatine is the combination of propylene glycol and ethanol. Another example is polyethylene glycol 300 (PEG 300) and polyethylene glycol 400 (PEG 400), which are generally considered to be among the safest organic cosolvents and are very commonly used in preclinical in vivo pharmacokinetic and efficacy studies due to their solubilizing capabilities and safety, when used in ratios up to 50% vol/vol in aqueous solution. A third example is glycerin (glycerol), which may be administered in combination with ethanol or propylene glycol, for example, up to 20% vol/vol. A fourth example is polysorbate 80, a surfactant commonly used in protein parenteral formulations and injectable solution formulations of small molecules. It can be used up to 20% in formulation alone, with pH modification or in combination with ethanol or propylene glycol.

The present invention also provides kits. In general, the kits comprise Nourexin-4 in an amount sufficient to treat at least one patient at least one time to reduce or eliminate inflammation caused by injury or disease. Typically, Nourexin-4 will be supplied in one or more containers, each container containing a sufficient amount of Nourexin-4 for at least one dosing of the patient. The kits can comprise other components, such as some or all of the components necessary to practice a method of the invention. The kits may contain a syringe for administering a dose of Nourexin-4. In embodiments, multiple doses of Nourexin-4 are provided in the kit, either all in a single container (e.g., a vial) or distributed among two or more containers. As the invention contemplates administering or delivering (used synonymously herein) of Nourexin-4 in liposomes, micellar carriers, and lipid emulsions, kits according to the invention may comprise liposomes, micellar carriers, and lipid emulsions, particularly when loaded with Nourexin-4.

In addition, kits can comprise isolated or purified (at least to some extent) Nourin. In such kits, the Nourin can be provided in amounts suitable for administration to a subject in need of enhancement of the natural inflammatory response. As discussed above, Nourin is a mediator of early inflammation. Reducing its presence can thus be used to reduce inflammation and the negative effects of excessive inflammation. On the other hand, in subjects where inflammation is insufficient to assist in the natural defense system, isolated Nourin can be supplied artificially to increase the inflammatory response.

EXAMPLES

The invention will be further explained by the following Examples, which are intended to be purely exemplary of the invention, and should not be considered as limiting the invention in any way.

Example 1

Release of the Leukocyte Chemotactic Factor Nourin from Epithelial Cells in Response to Influenza Virus Infection This study was performed to determine whether epithelial MDCK cells grown in culture release Nourin in response to injury induced by laboratory adapted influenza virus. For these experiments, MDCK cells were infected with the laboratory influenza virus H1N1 (PR8) for 1, 3, 6, 12, and 24 hours. Control cells were incubated with culture media only. At various time points (1-24 hours), supernatant solutions were collected and tested for the presence and levels of chemotactic activity using a modified chemotaxis chamber as a functional assay for chemotactic factors. Neutrophils isolated from human peripheral blood were used as the migratory cells.

Results from these experiments showed significant chemotactic activity in supernatant solutions collected from H1N1 infected cells (diamonds) compared to control cells grown in culture without the virus (rectangles) (FIG. 1). These data suggest the ability of epithelial cells to quickly release (within first 6 hours) high levels of chemotactic factor in response to influenza viral infection. Further, the activity remained elevated for an additional 18 hours of incubation.

Example 2

Nourexin-4 Inhibits f-MLP and the *S. aureus*-derived PSM3a Chemotactic Activity In Vitro In this study, Nourexin-4, an inhibitor of Nourin, was tested for its ability to inhibit two bacterial-derived formyl peptides: formyl-Methionine-Leucine-Phenylalanine (f-MLP) and PSM3a. f-MLP was discovered as a bacterial product with leukocyte chemotactic activity (cell recruitment) for phagocytic leukocytes (neutrophils and monocytes). PSM3a is one of a number of formyl peptides secreted by *S. aureus* bacteria that is able to recruit and activate leukocytes and subsequently induce overactive host inflammatory response, organ failure, and death in mice.

The ability of Nourexin-4 to inhibit neutrophil chemotaxis in vitro was tested using f-MLP (FIG. 2) and PSM3a (FIG. 3). For these studies, a standard Neuroprobe chemotaxis system (Gaithersburg, Md.) and human peripheral neutrophils as indicator cells were used.

These experiments illustrate the strong neutrophil chemotactic activity induced in vitro by f-MLP and PSM3a. As indicated in FIG. 2, Nourexin-4 at $5\times10^{-5}$ M and $5\times10^{-4}$M completely blocked neutrophil chemotaxis induced by f-MLP. Similarly, at $5\times10^{-4}$ M, Nourexin-4 completely blocked neutrophil chemotaxis induced by the *S. aureus*-derived PSM3a, and partially blocked chemotaxis at $5\times10^{-5}$ M (FIG. 3). For the experiments reported herein, Nourexin-4 was dissolved in ($10^{-2}$ M) DMSO then diluted in saline to various concentrations.

Example 3

Nourexin-4 Inhibits fMLP and Influenza-Induced Nourin in Cell Culture f-MLP, which is also referred to as Nourin related peptide (NRP-1), is an extremely potent inducer of human leukocyte chemotaxis in vitro. In this experiment, the ability of Nourexin-4 ($5\times10^{-7}$ M, $5\times10^{-6}$ M, $5\times10^{-5}$ M, $5\times10^{-4}$ M) to inhibit chemotaxis was tested in human leukocyte cells (FIG. 4). As can be seen from the results, Nourexin-4 was able to block induction of chemotaxis by f-MLP at concentrations starting at $10^{-7}$ M.

To test the ability of Nourexin-4 to inhibit the chemotactic activity of Nourin released by cells infected with the influenza virus, H1N1 (PR8) infected MDCK cells were assayed after 1, 3, 6, 12, and 24 hours of infection (FIG. 5). Each H1N1 infected cell supernatant was assayed both in the presence or absence of Nourexin-4 ($5\times10^{-6}$ M). Supernatant solutions were evaluated both undiluted (neat) and diluted 1/10 in Hanks balance salt solution. As can be seen in FIG. 5, the undiluted MDCK-PR8 supernatant sample had immediate and high chemotactic activity (MDCK-PR8 Supt). Chemotactic activity was also detected in the 1/10 diluted samples of the culture supernatants (1/10 MDCK-PR8 Supt). The addition of $5\times10^{-6}$ M Nourexin-4 resulted in a dramatic loss of chemotactic activity at all time points in both the undiluted (MDCK-PR8 Supt+Nourexin-4) and the 1/10 diluted (1/10 MDCK-PR8 Supt+Nourexin-4) supernatant solutions. These results indicate that the chemotactic factor released by epithelial cells in response to H1N1 viral infection is Nourin. These data not only confirm the expression of Nourin in culture supernatant solutions from influenza virus infected cells, but also demonstrate that Nourexin-4 is a potent inhibitor of Nourin.

Example 4

Nourexin-4 Inhibition of Chemotactic Activity in Mouse Serum Obtained from Mice after H1N1 Influenza Virus Infection The studies described above clearly demonstrated that H1N1 influenza virus infection of MDCK cells results in expression of Nourin into the cell culture supernatant shortly after viral challenge and that chemotactic activity induced by viral Nourin is inhibited by Nourexin-4. To determine if chemotactic activity was present early in the blood of mice infected with H1N1 virus, and if so, whether Nourexin-4 was capable of inhibiting chemotactic activity in the blood of influenza infected mice, four mice were infected with H1N1 influenza virus (designated WSN-1 thru WSN-4), and four mice received sham treatment without H1N1 virus (designated Mock-1 thru Mock-4). Balb/C female, 5 weeks old were used in these studies. For the influenza infected group, mice were anesthetized with isofluorane and intranasally inoculated with 10 MLD50 of WSN (mouse adapted A/WSN/33 strain, H1N1) in 50 ul PBS. Six hours post virus or sham treatment, blood samples were collected from both WSN and Mock mice and processed for serum. The resulting serum was stored at −70° C. until it was used for chemotaxis assays to determine LCF activity and the ability of Nourexin-4 to inhibit that activity. For this study, the standard Neuroprobe chemotaxis system (Gaithersburg, Md.) and human PMNs as indicator cells were used. Serum samples from the four Mock mice or the four WSN virus infected mice were diluted in Hanks balanced salt solution (HBSS) at a dilution of 1/7, with or without $5\times10^{-6}$ M Nourexin-4. The resulting serum samples (with and without Nourexin-4) were assayed for chemotactic activity as described above.

Results from these studies show that serum from mice infected with the H1N1 influenza virus (WSN) contained significantly more chemotactic activity when compared to non-virus infected mice (sham) (FIG. 6). Additionally, the majority of this virus induced LCF activity is clearly inhibited with Nourexin-4.

The present data demonstrate for the first time that Nourin is rapidly released by cultured epithelial cells infected with influenza virus and that virus-induced Nourin can be detected as early as six hours in mouse serum. In addition, this study has shown that the majority of this influenza-induced Nourin chemotactic activity can be inhibited by the formyl peptide specific competitive antagonist Nourexin-4 (cyclosporin H) which further confirms that Nourin is an endogenous formyl peptide that acts primarily on FPR. Because Nourin recruits and activates leukocytes into infected tissues leading to lung inflammation and tissue damage and it also stimulates the release of high levels of cytokine storm mediators by monocytes and neutrophils, blocking Nourin activity with Nourexin-4 after influenza infection will not only inhibit lung inflammation and tissue damage but will also reduce the expression of circulating cytokine storm mediators. Therefore, the invention provides methods to combat excessive inflammation, protect patients from damaging effects of the virus-induced host inflammatory response, and thus decrease morbidity and mortality in influenza-infected patients.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

The invention claimed is:

1. A composition comprising a nano-lipid emulsion of Nourexin-4 and lipid, wherein the lipid comprises an oil phase that comprises one or more of:
    oleyl diglycerides, oleyl triglycerides, linoleyl diglycerides, and linoleyl triglycerides, wherein this group is not less than 20% by weight of the total nano-lipid emulsion.

2. The composition of claim 1, wherein the nano-lipid emulsion further comprises phosphatidylcholine, cholesterol, and triolein.

3. The composition of claim 2, wherein the nano-lipid emulsion further comprises phosphatidylserine, phosphatidylethanolamine, dimyristoylphosphatidylglycerol, or any combination thereof.

4. The composition of claim 1, wherein the nano-lipid emulsion further comprises phosphatidylcholine, cholesterol, phosphatidylethanolamine, and PEGylated vitamin E.

5. The composition of claim 1, wherein the nano-lipid emulsion further comprises phosphatidylcholine, cholesterol, ganglioside, and triolein.

6. The composition of claim 1, wherein the nano-lipid emulsion further comprises phosphatidylcholine, cholesterol, PEG2000-5000-phosphatidylethanolamine, and triolein.

7. The composition of claim 1, wherein the nano-lipid emulsion further comprises cholesterol and/or cholesteryl amines; and vitamin E.

8. The composition of claim 1, wherein the nano-lipid emulsion further comprises benzyl alcohol and/or benzyl benzoate; and vitamin E.

* * * * *